United States Patent [19]

Rigbi et al.

[11] Patent Number: 5,182,113
[45] Date of Patent: Jan. 26, 1993

[54] FACTOR XA INIBITOR FROM LEECH AND PHARMACEUTICAL COMPOSITIONS CONTAINING SAME

[75] Inventors: Meir Rigbi, Jerusalem, Israel; Craig M. Jackson, Grosse Pointe Farms, Mich.

[73] Assignee: Bio-Technology General Corp., New York, N.Y.

[21] Appl. No.: 370,601

[22] Filed: Jun. 23, 1989

[30] Foreign Application Priority Data

Jun. 24, 1988 [IL] Israel ......................................... 86856

[51] Int. Cl.$^5$ ............................................. A61K 35/62
[52] U.S. Cl. .................................... 424/537; 424/550; 530/855; 514/21
[58] Field of Search ....................... 424/520, 550, 537; 530/855; 514/2, 21

[56] References Cited

U.S. PATENT DOCUMENTS

| | | | |
|---|---|---|---|
| 4,588,587 | 5/1986 | Gasic | 424/95 |
| 4,791,100 | 12/1988 | Kramer et al. | 514/12 |
| 4,832,849 | 5/1989 | Cardin | 514/12 |

FOREIGN PATENT DOCUMENTS 0346894 12/1989 European Pat. Off. .

OTHER PUBLICATIONS

Condra et al., Thrombosis and Haemostatis 61(3):437–441 (1989) (Exhibit C).
Baskova, I. P.; Nikonov, G. I. "Antithrombotic effect of salivary gland secretion and of other preparations from *Hirudo medicinalis* after intravenous and peroral administrations into rats", *Chemical Abstracts* 106 (No. 9), Abstract No. 60996w (Mar. 2, 1987) and *Vopr. Med. Khim.* 32(6): 90–93 (1986) (Russ.).
Gasic, G. J. et al., Cancer Res. 43: 1633–1636 (1983).
Gasic, G. J. et al., Cancer Res. 44: 5670–5676 (1984).
Abstract 110: 185955w, Gasic, G. J. et al. (1986).

*Primary Examiner*—Douglas W. Robinson
*Assistant Examiner*—Jean C. Witz
*Attorney, Agent, or Firm*—John P. White

[57] ABSTRACT

A novel anticoagulant/modulator factor isolated from the saliva of the medicinal leech *Hirudo medicinalis*, specifically inhibiting bovine Xa factor but not inhibiting bovine thrombin.

9 Claims, 2 Drawing Sheets

FACTOR XA INIBITOR FROM LEECH AND PHARMACEUTICAL COMPOSITIONS CONTAINING SAME

The present invention concerns a novel anticoagulant factor from the saliva of the medicinal leech *Hirudo medicinalis*, pharmaceutical compositions for modifying blood coagulation containing the same and methods of modifying blood coagulation thereby.

DETAILED DESCRIPTION OF THE INVENTION

Figure 1:
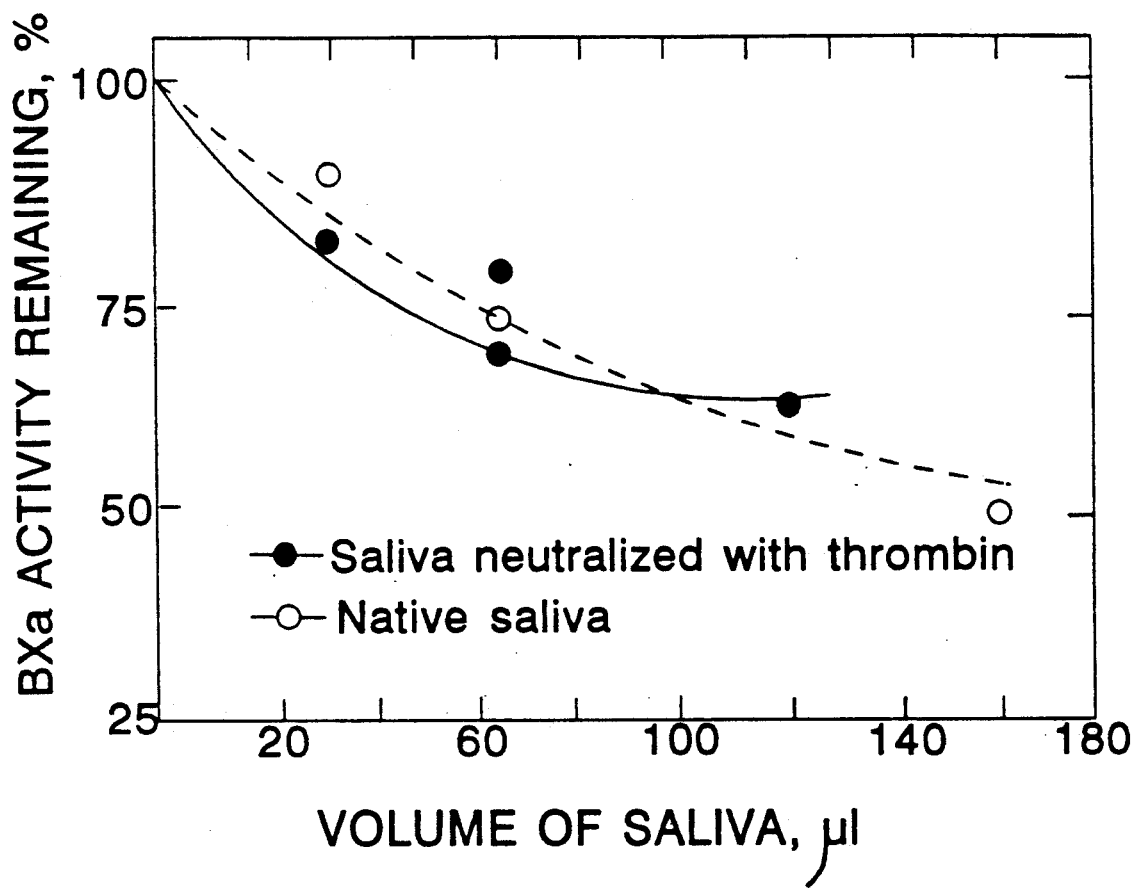
FIG. 1 inhibition of bovine Xa activity by native leech saliva and saliva neutralized with thrombin. Incremental amounts of native saliva and thrombin-treated saliva were added to bovine Xa. The percent remaining activity of bovine Xa after addition of native saliva is indicated by the dashed line. The percent remaining activity of bovine Xa after addition of thrombin-treated saliva is indicated by the solid line.

More particularly, the present invention concerns a novel anticoagulant factor from the saliva of the medicinal leech, *Hirudo medicinalis*, said factor specifically inhibiting bovine Factor Xa factor but not thrombin. It is different from hirudin, the main anticoagulant factor in the said saliva, which inhibits thrombin, but as became apparent, does not inhibit bovine F.Xa.

Another important characterizing property of the novel fraction subject of the present application is, that it is a mild inhibitor, in contrast to hirudin, and also in contrast to heparin, which accelerates the action of antithrombin and is presently therapeutically used. This property of the isolated factor may be termed a modulating action, opening up the possibility of a therapeutic use in cases where a more controllable or milder inhibition of blood coagulation is desirable. An indication that the novel factor is a mild inhibitor, or a modulator, of blood coagulation is that it is capable of slowing down the inactivation of the bovine F.Xa induced by heparin and antithrombin.

The proof that the novel factor is in principle different from hirudin is that the leech saliva treated with an excess of bovine thrombin inhibits the action of bovine F.Xa on a suitable substrate, and as a complementary check, saliva treated with an excess of bovine F.Xa inhibits the action of bovine thrombin, the action of hirudin being specific to thrombin.

The isolation of the novel factor is based on the same principle, that is, adsorption of the same on bovine F.Xa, suitably immobilized, and subsequent elution. More particularly, a suitable adsorbent is Affi-Gel, equilibrated with F.Xa, and, as eluent, weak acids at pH of about 2.9 are suitable. The substance ma be eluted by hydrochloric acid but is rapidly destroyed by the high acidity. Acetic acid is more suitable. The molecular weight of the anticoagulant factor subject of the present invention is between 10 and 30 kD, as it passes an ultrafilter with a cut-off point of 30kD and is essentially retained on an ultrafilter with a cut-off point of 10 kD.

Regarding the methods, synthetic substrates having a chromogenic end group such as pNA (para- nitroanilide) are preferably used, enabling easy monitoring of the progress of the coagulation by spectrophotometer methods. The substrates used were, in particular, N-methoxycarbonyl-D-cyclohexylGly-Gly-L-Arg-pNA (CHG), (Pentapharm Ltd., Switzerland and Boehringer Mannheim GmbH, F.R.G.), Tos-Gly-L-Pro-L-Arg-pNA (Chromozym TH, resp. CZTH), (Pentapharm Ltd., Switzerland and Boehringer Mannheim GmbH, F.R.G.) and D-Ile-L-Pro-L-Arg-pNA (S-2288, Kabi Peptide Research, Sweden) (pNA designates p-nitroalanine). The reactions were monitored at 405 nm in a spectrophotometer connected to a computer and the kinetic parameter were calculated from the appropriate extinction coefficients by a Jackson-Labanowski linear regression program. The measurements were carried out in disposable polystyrene cuvettes at pH of 7.8 and a temperature of 25° C. Known values (Lottenberg, R. et al., Biochim-Biophys. Acta 874 (1986) pp. 326–335; Lottenberg, R. et al. *ibid* 742 (1983) pp. 539–557 (bovine thrombin) of the parameters $K_m$ and $K_{cat}$ were used for the determination of F.Xa, thrombin and their inhibition.

Figure 2:
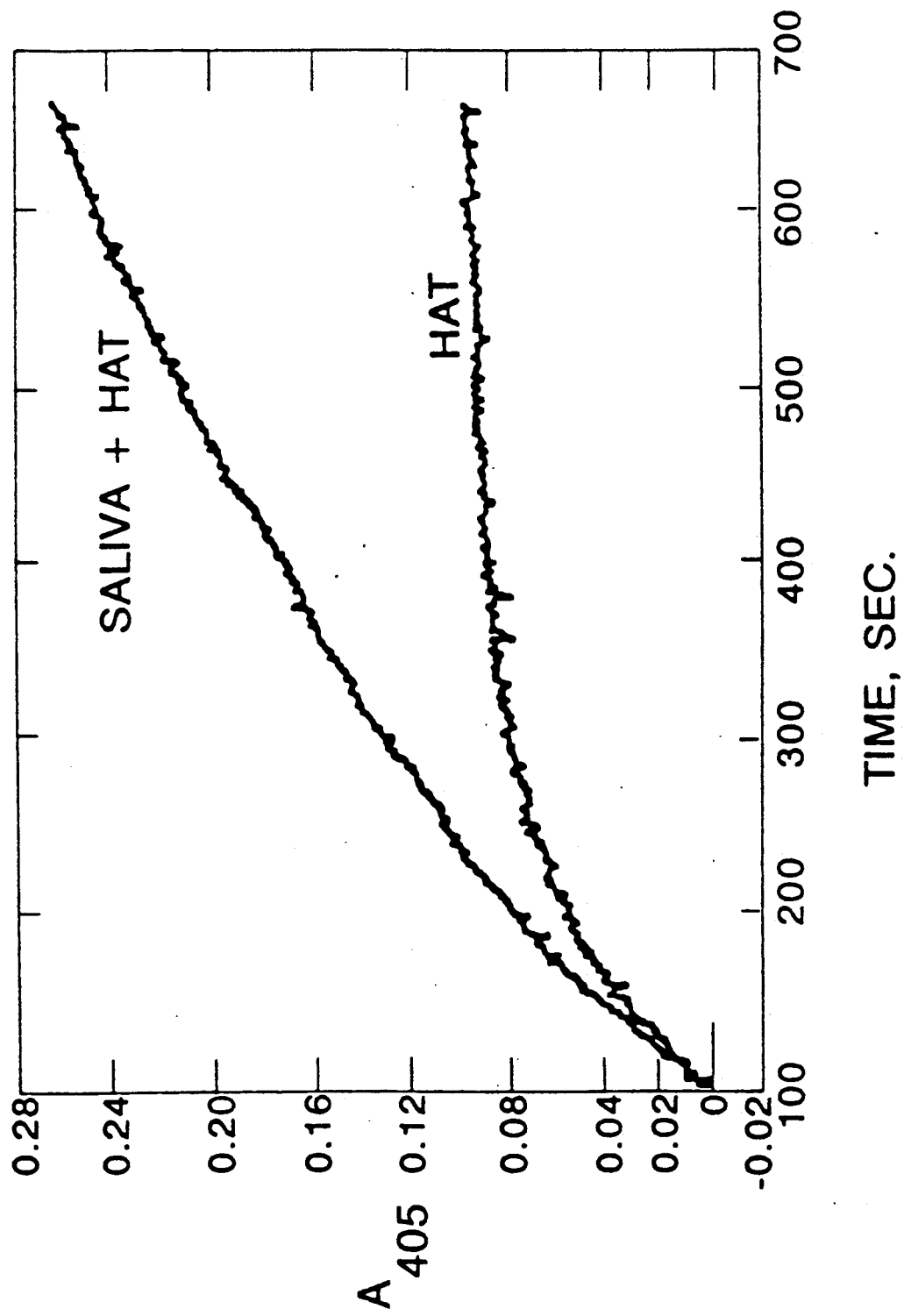
FIG. 2 time course of bovine Xa inactivation by heparinantithrombin (HAT) in the absence and presence of leech saliva. The top line illustrates the rate of inactivation of bovine Xa by HAT in the presence of leech saliva. The bottom line illustrates the rate of inactivation of bovine Xa by HAT in the absence of leech saliva.

An important characteristic of the factor subject of the present invention, which may differentiate the same from other known anticoagulants such as heparin and also hirudin, is its dose-dependent mod of action. When incremental amounts of saliva, both native and more particularly treated with thrombin, were added to bovine Xa, the activity of the same at first dropped sharply, but afterwards tended to level off asymptotically at 50 to 60%. This effect is essentially the same with thrombin-treated saliva. This result is illustrated graphically in appended FIG. 1. An important characteristic of the factor subject of the present application, already referred to above, is the slowing down of the rate of inactivation of bovine F.Xa by heparin-antithrombin. FIG. 2 illustrates this by a comparative plot of the inactivation of BXa by heparinantithrombin, in the absence and presence of saliva. The possible importance of this phenomenon is already discussed above.

The inhibitor/modulator (henceforth designated XaM) subject of the present invention is a mixed type inhibitor, which means that either the enzyme-inhibitor complex (EI) may react with the substrate, or the enzyme-substrate complex (ES) may react with the inhibitor (I). This view is strengthened by the fact that the inhibitor/modulator, bound to bovine F.Xa immobilized on a suitable column, cannot be eluted by D-Phe-Pipecolyl-L-Arg-pNa (S2238-Kabi Peptide) which has a high affinity ($K_m$, 46.9μM) and a low catalytic rate constant ($K_{cat}$ 0.681 s$^{-2}$) for F.Xa.

The inhibitor/modulator of the present invention may be isolated from the saliva by adsorption on an Affi-Gel column on which bovine F.Xa is fixed and subsequent elution with acetic acid. Hirudin was not adsorbed on said gel. Affi-Gel 10 is used, which is a derivatized ross-linked agarose containing a 10-atom spacer arm esterified to N-hydroxysuccinimide. The capacity of this gel is 10 micromoles/ml.

An example of isolating the inhibitor/modulator factor of the present invention comprises the following steps:

1. Coupling. To 1ml washed Affi-Gel 10 in a minicolumn were added 2ml of a dialyzed BXa solution (40 nmoles) in 0.05 M Hepes/0.1 M NaCl buffer pH 7.5. The column was shaken for 2 h at room temp. The supernatant was then run off the column, which was not allowed to dry. Ninety four percent of the BXa load was bound to the gel.

2. Neutralization of remaining N-hydroxysuccinimide groups.

One ml of a mixture of 4 parts ethanolamine pH 8 and 6 parts 0.01M Tris/0.01M Hepes/0.1M NaCl/0.1% polyethylene glycol buffer pH 7.8 were added. Shaking for 1 h at room temperature was followed by three washes with same buffer.

3. Affinity binding of XaM. Leech saliva (40 ml, 305 pmoles XaM) was adjusted to pH 7.9 by adding 1% v/v 1M Tris pH 8 and was passed through the column. Ninety two percent of the XaM was bound to the gel. Hirudin was not bound.

4. Elution of XaM. The column was shaken with successive 1 ml volumes of 0.1M acetic acid (pH 2.9) which were neutralized on elution with 1 M $NH_4OH$. Recovery of bound XaM was 72.5 percent (203 pmoles).

The inhibitor/modulator factor of the present invention is useful in the treatment of thromboembolic diseases owing to its action of inhibiting the coagulation enzynmes and at the same time slowing down the rate of inactivation of other anticoagulants, maintaining these two in balance. The advantages over heparin, the most commonly presently used anticoagulant are that heparin increases the risk of hemorrhage and interferes with the function of platelets. The present Xa modulator bears a strong resemblance to antistasin, the antimetastatic inhibitor which Tuszynski, Gasic and Gasic (The Journal of Biological Chemistry 262/20 1987, 9718–23) isolated from the Mexican leech, *Haementeris officinalis*. Both proteins are similar in molecular weight, in their specificity towards Xa and in the fact that the dose-response curve flattens out at about 50% remaining BXa activity. However, these two leech species belong to different orders in the classification scheme. The relationship between the genera Haementeria and Hirudo is best given by the following scheme (Roy T. Sawyer, "Leech Biology and Behaviour, Vol. II", Oxford Science Publications, 1986):

| Class: | Hirudinea | |
| --- | --- | --- |
| Order: | Rynchobdellida (protrusible proboscis) | Arynchobdellida (pharynx, no proboscis, with or without jaws) |
| Family: | Glossiphoniidae | Hirudinidae (jawed) |
| Genus: | Haementeria | Hirudo |

Proteins derived from leeches belonging to said different orders may be dissimilar in both identity and properties.

The invention is also concerned with pharmaceutical composition comprising a active ingredient the anticoagulant/modulator factor of the present invention with a suitable pharmaceutically acceptable carrier or diluent. More particularly the pharmaceutical compositions of the present invention are intended for modifying blood coagulation. Still more particularly the pharmaceutical compositions of the present invention are intended for modifying blood coagulation associated with thromboembolic diseases.

The preparations according to the present invention may be administered orally or parenterally in dosage unit formulations containing conventional non-toxic pharmaceutically acceptable carriers, diluents, adjuvants and vehicles as desired. The term parenteral as used herein includes subcutaneous, intravenous intraartilcular and intratechal injection an infusion techniques. Dosage unit preparations may contain daily required amounts of the purified compositions of matter of the present invention or submultiples thereof to make up the desired dose. The specific therapeutically effective does level for any particular patient will depend upon a variety of factors including the activity material employed, the age, body weight, general health, sex, diet, time of administration, route of administration, rate of excretion, etc.

As used herein, the term "pharmaceutically acceptable carrier" means an inert, non-toxic solid or liquid filler, diluent or encapsulating material, not reacting with the active ingredients according to the invention. These carriers are known to the man versed in the art. Wetting agents and emulsifiers, as well as release agents, coating agents and preservatives can also be present in the preparations of the invention. The amount of active ingredient that may be combined with the carrier materials to produce a single dosage form will vary, depending upon the patient treated and the particular mode of administration.

Methods of modifying blood coagulation, more particularly when associated with thromboembolic disorders, and treating and preventing the said pathological conditions by administering to a subject any of the said pharmaceutical preparations are also provided by the present invention.

What is claimed is:

1. A protein isolated from the medicinal leech *Hirudo medicinalis* which specifically inhibits bovine Factor Xa but does not inhibit bovine thrombin and has a molecular weight in the range of 10–30 kD.

2. The protein of claim 1 being an inhibitor of the mixed type, not eluted by a substance having a high affinity ($K_m$) of about 47 $\mu$M and a catalytic rate constant ($k_{cat}$) of about 0.681 $s^{-1}$ for bovine Factor Xa, said polypeptide being adsorbed on a suitable column comprising immobilized bovine Factor Xa.

3. The protein of claim 2 being an inhibitor of the mixed type not eluted by D-Phe-Pipecolyl-L-Arg-pNa when adsorbed on a suitable column comprising immobilized bovine Factor Xa.

4. A pharmaceutical composition for modifying blood coagulation comprising as the active ingredient the protein of claim 1 present in a therapeutically effective amount and a pharmaceutically acceptable carrier.

5. A method of modifying blood coagulation by administering to a patient a therapeutically effective amount of a composition according to claim 4.

6. A method of modifying blood coagulation associated with thromboembolic diseases by administering to a patient a therapeutically effective amount of a composition according to claim 4.

7. A method of isolating the protein of claim 1 comprising passing saliva of the medicinal leech *Hirudo medicinalis* through suitably immobilized bovine Factor Xa, subsequently eluting said protein with acid and then neutralizing the elute.

8. The method according to claim 7 wherein the bovine Factor Xa is immobilized by being coupled to an insoluble solid support.

9. The method of claim 8 wherein said solid support is an Affi-Gel 10 column and the protein is eluted with acetic acid.

* * * * *

UNITED STATES PATENT AND TRADEMARK OFFICE
CERTIFICATE OF CORRECTION

PATENT NO. : 5,182,113
DATED : January 26, 1993
INVENTOR(S) : Meir Rigbi, et al.

It is certified that error appears in the above-identified patent and that said Letters Patent is hereby corrected as shown below:

Column 1, line 64, "ma" should read --may--.

Column 2, line 14, "p-nitroalanine" should read --p-nitroaniline--.

Column 2, line 30, "mod" should read --mode--.

Column 2, line 61, "ross-linked" should read --cross-linked--.

Column 3, line 25, "enzynmes" should read --enzymes--.

Column 3, line 57, "a" should read --as--.

Column 4, line 4, "an" should read --and--.

Column 4, line 9, "does" should read --dose--.
Column 4,
Claim 7, line 5, "elute" should read --eluate--.

Signed and Sealed this

Nineteenth Day of July, 1994

Attest:

BRUCE LEHMAN

*Attesting Officer*   *Commissioner of Patents and Trademarks*